(12) United States Patent
Georges

(10) Patent No.: US 11,497,616 B2
(45) Date of Patent: Nov. 15, 2022

(54) INTERBODY DEVICE WITH OPENING TO ALLOW PACKING GRAFT AND OTHER BIOLOGICS

(71) Applicant: DePuy Synthes Products, Inc., Raynham, MA (US)

(72) Inventor: Bacem Georges, Franklin, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/238,561

(22) Filed: Jan. 3, 2019

(65) Prior Publication Data

US 2019/0133785 A1     May 9, 2019

Related U.S. Application Data

(63) Continuation of application No. 13/673,061, filed on Nov. 9, 2012, now Pat. No. 10,182,921.

(51) Int. Cl.
*A61F 2/44* (2006.01)
*A61F 2/30* (2006.01)
*A61F 2/46* (2006.01)
*A61B 17/86* (2006.01)
*A61F 2/28* (2006.01)

(52) U.S. Cl.
CPC .......... *A61F 2/4455* (2013.01); *A61B 17/86* (2013.01); *A61F 2/30744* (2013.01); *A61F 2/4611* (2013.01); *A61F 2002/2835* (2013.01); *A61F 2002/30482* (2013.01); *A61F 2002/30904* (2013.01)

(58) Field of Classification Search
CPC ............ A61F 2/442; A61F 2/4455–447; A61F 2002/4629; A61F 2/4611
See application file for complete search history.

(56) References Cited

U.S. PATENT DOCUMENTS

| | | | |
|---|---|---|---|
| 1,636,636 A | 7/1927 | Humble | |
| 1,677,337 A | 7/1928 | Grove | |
| 2,304,703 A | 12/1942 | O'Leary | |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |

(Continued)

FOREIGN PATENT DOCUMENTS

| | | |
|---|---|---|
| CN | 201244104 Y | 5/2009 |
| CN | 101951847 A | 1/2011 |

(Continued)

OTHER PUBLICATIONS

Vandorpe, "Biodegradable Polyphosphazenes for Biomedical Applications", The Handbook of Biodegradable Polymers, edited by Domb et al., Hardwood Academic Press, 1997, pp. 161-182.

(Continued)

*Primary Examiner* — Nicholas J Plionis
(74) *Attorney, Agent, or Firm* — BakerHostetler

(57) ABSTRACT

An intervertebral fusion device having a cage having an opening or window in its front wall that allows for the insertion of bone graft therethrough after the cage has been placed into the disc space. The device further has a faceplate that covers the front wall of the cage and provides features for securing bone screws to the adjacent vertebral bodies.

12 Claims, 8 Drawing Sheets

(56) References Cited

U.S. PATENT DOCUMENTS

| | | | |
|---|---|---|---|
| 4,205,399 | A | 6/1980 | Jamiolkowski et al. |
| 4,208,511 | A | 6/1980 | Jamiolkowski et al. |
| 4,743,256 | A | 5/1988 | Brantigan |
| 4,904,261 | A | 2/1990 | Dove et al. |
| 4,946,378 | A | 8/1990 | Hirayama et al. |
| 4,955,908 | A | 9/1990 | Frey et al. |
| 5,041,113 | A | 8/1991 | Biedermann et al. |
| 5,123,926 | A | 6/1992 | Pisharodi |
| 5,147,361 | A | 9/1992 | Ojima et al. |
| 5,209,751 | A | 5/1993 | Farris et al. |
| 5,306,308 | A | 4/1994 | Gross et al. |
| 5,352,231 | A | 10/1994 | Brumfield et al. |
| 5,391,170 | A | 2/1995 | McGuire et al. |
| 5,395,372 | A | 3/1995 | Holt et al. |
| 5,397,364 | A * | 3/1995 | Kozak ............ A61B 17/025 623/17.11 |
| 5,443,514 | A | 8/1995 | Steffee |
| 5,443,515 | A | 8/1995 | Cohen et al. |
| 5,464,407 | A | 11/1995 | McGuire |
| 5,464,929 | A | 11/1995 | Bezwada et al. |
| 5,499,986 | A | 3/1996 | Dimarco |
| 5,529,580 | A | 6/1996 | Kusunoki et al. |
| 5,534,031 | A | 7/1996 | Matsuzaki et al. |
| 5,578,034 | A | 11/1996 | Estes |
| 5,591,166 | A | 1/1997 | Bernhardt et al. |
| 5,595,751 | A | 1/1997 | Bezwada et al. |
| 5,597,579 | A | 1/1997 | Bezwada et al. |
| 5,601,553 | A | 2/1997 | Trebing et al. |
| 5,607,687 | A | 3/1997 | Bezwada et al. |
| 5,609,636 | A | 3/1997 | Kohrs et al. |
| 5,618,552 | A | 4/1997 | Bezwada et al. |
| 5,620,458 | A | 4/1997 | Green et al. |
| 5,620,698 | A | 4/1997 | Bezwada et al. |
| 5,645,598 | A | 7/1997 | Brosnahan, III |
| 5,645,850 | A | 7/1997 | Bezwada et al. |
| 5,648,088 | A | 7/1997 | Bezwada et al. |
| 5,662,655 | A | 9/1997 | Laboureau et al. |
| 5,676,666 | A | 10/1997 | Oxland et al. |
| 5,698,213 | A | 12/1997 | Jamiolkowski et al. |
| 5,700,583 | A | 12/1997 | Jamiolkowski et al. |
| 5,713,899 | A | 2/1998 | Marnay et al. |
| 5,716,415 | A | 2/1998 | Steffee |
| 5,755,796 | A | 5/1998 | Ibo et al. |
| 5,776,196 | A | 7/1998 | Matsuzaki et al. |
| 5,779,707 | A | 7/1998 | Bertholet et al. |
| 5,785,713 | A | 7/1998 | Jobe |
| 5,788,698 | A | 8/1998 | Savornin |
| 5,797,912 | A | 8/1998 | Runciman et al. |
| 5,797,918 | A | 8/1998 | McGuire et al. |
| 5,800,435 | A | 9/1998 | Errico et al. |
| 5,800,440 | A | 9/1998 | Stead |
| 5,859,150 | A | 1/1999 | Jamiolkowski et al. |
| 5,888,223 | A | 3/1999 | Bray, Jr. |
| 5,893,889 | A | 4/1999 | Harrington |
| 5,904,689 | A | 5/1999 | Jonjic |
| 5,913,860 | A | 6/1999 | Scholl |
| 6,039,761 | A | 3/2000 | Li et al. |
| 6,049,026 | A | 4/2000 | Muschler |
| 6,056,749 | A | 5/2000 | Kuslich |
| 6,066,175 | A | 5/2000 | Henderson et al. |
| 6,086,593 | A | 7/2000 | Bonutti |
| 6,093,205 | A | 7/2000 | McLeod et al. |
| 6,099,531 | A | 8/2000 | Bonutti |
| 6,106,557 | A | 8/2000 | Robioneck et al. |
| 6,117,174 | A | 9/2000 | Nolan |
| 6,120,503 | A | 9/2000 | Michelson |
| 6,126,689 | A | 10/2000 | Brett |
| 6,127,597 | A | 10/2000 | Beyar et al. |
| 6,139,550 | A | 10/2000 | Michelson |
| 6,156,037 | A | 12/2000 | Lehuec et al. |
| 6,159,211 | A | 12/2000 | Boriani et al. |
| 6,159,244 | A | 12/2000 | Suddaby |
| 6,174,311 | B1 | 1/2001 | Branch et al. |
| 6,179,875 | B1 | 1/2001 | Von Strempel |
| 6,190,414 | B1 | 2/2001 | Young et al. |
| 6,193,757 | B1 | 2/2001 | Foley et al. |
| 6,200,306 | B1 | 3/2001 | Klostermeyer et al. |
| 6,206,922 | B1 | 3/2001 | Zdeblick et al. |
| 6,224,602 | B1 | 5/2001 | Hayes |
| 6,224,631 | B1 | 5/2001 | Kohrs |
| 6,231,610 | B1 | 5/2001 | Geisler |
| 6,235,059 | B1 | 5/2001 | Benezech et al. |
| 6,306,170 | B2 | 10/2001 | Ray |
| 6,330,845 | B1 | 12/2001 | Meulink |
| 6,336,928 | B1 | 1/2002 | Guerin et al. |
| 6,342,055 | B1 | 1/2002 | Eisermann et al. |
| 6,342,074 | B1 | 1/2002 | Simpson |
| 6,364,880 | B1 | 4/2002 | Michelson |
| 6,368,351 | B1 | 4/2002 | Glenn et al. |
| 6,375,462 | B2 | 4/2002 | Holweg et al. |
| 6,387,130 | B1 | 5/2002 | Stone et al. |
| 6,395,031 | B1 | 5/2002 | Foley et al. |
| 6,406,478 | B1 | 6/2002 | Kuo |
| 6,409,766 | B1 | 6/2002 | Brett |
| 6,413,278 | B1 | 7/2002 | Marchosky |
| 6,423,063 | B1 | 7/2002 | Bonutti |
| 6,428,575 | B2 | 8/2002 | Koo et al. |
| 6,432,106 | B1 | 8/2002 | Fraser |
| 6,447,544 | B1 | 9/2002 | Michelson |
| 6,447,546 | B1 | 9/2002 | Bramlet et al. |
| 6,454,769 | B2 | 9/2002 | Wagner et al. |
| 6,461,359 | B1 | 10/2002 | Tribus et al. |
| 6,471,724 | B2 | 10/2002 | Zdeblick et al. |
| 6,488,710 | B2 | 12/2002 | Besselink |
| 6,508,818 | B2 | 1/2003 | Steiner et al. |
| 6,558,387 | B2 | 5/2003 | Errico et al. |
| 6,558,423 | B1 | 5/2003 | Michelson |
| 6,562,073 | B2 | 5/2003 | Foley |
| 6,565,570 | B2 | 5/2003 | Sterett et al. |
| 6,572,619 | B2 | 6/2003 | Santilli |
| 6,579,290 | B1 | 6/2003 | Hardcastle et al. |
| 6,579,321 | B1 | 6/2003 | Gordon et al. |
| 6,592,624 | B1 | 7/2003 | Fraser et al. |
| 6,602,257 | B1 | 8/2003 | Thramann |
| 6,629,998 | B1 | 10/2003 | Lin |
| 6,679,915 | B1 | 1/2004 | Cauthen |
| 6,682,563 | B2 | 1/2004 | Scharf |
| 6,695,846 | B2 | 2/2004 | Richelsoph et al. |
| 6,730,125 | B1 | 5/2004 | Lin |
| 6,730,127 | B2 | 5/2004 | Michelson |
| 6,733,531 | B1 | 5/2004 | Trieu |
| 6,736,850 | B2 | 5/2004 | Davis |
| 6,743,257 | B2 | 6/2004 | Castro |
| 6,745,255 | B2 | 6/2004 | Yen et al. |
| 6,761,738 | B1 | 7/2004 | Boyd |
| 6,770,096 | B2 | 8/2004 | Bolger et al. |
| 6,773,437 | B2 | 8/2004 | Ogilvie et al. |
| 6,776,781 | B1 | 8/2004 | Uwaydah |
| 6,805,714 | B2 | 10/2004 | Sutcliffe |
| 6,808,537 | B2 | 10/2004 | Michelson |
| 6,824,564 | B2 | 11/2004 | Crozet |
| 6,824,565 | B2 | 11/2004 | Muhanna et al. |
| 6,833,006 | B2 | 12/2004 | Foley et al. |
| 6,835,208 | B2 | 12/2004 | Marchosky |
| 6,837,905 | B1 | 1/2005 | Lieberman |
| 6,849,093 | B2 | 2/2005 | Michelson |
| 6,890,335 | B2 | 5/2005 | Grabowski et al. |
| 6,890,355 | B2 | 5/2005 | Michelson |
| 6,945,973 | B2 | 9/2005 | Bray |
| 6,972,019 | B2 | 12/2005 | Michelson |
| 6,974,479 | B2 | 12/2005 | Trieu |
| 6,974,480 | B2 | 12/2005 | Messerli et al. |
| 6,984,234 | B2 | 1/2006 | Bray |
| 7,001,385 | B2 | 2/2006 | Bonutti |
| 7,033,394 | B2 | 4/2006 | Michelson |
| 7,041,135 | B2 | 5/2006 | Michelson |
| 7,044,971 | B2 | 5/2006 | Suddaby |
| 7,056,341 | B2 | 6/2006 | Crozet |
| 7,063,491 | B2 | 6/2006 | French |
| 7,070,598 | B2 | 7/2006 | Lim et al. |
| 7,077,864 | B2 | 7/2006 | Byrd et al. |
| 7,087,055 | B2 | 8/2006 | Lim et al. |
| 7,112,222 | B2 | 9/2006 | Fraser et al. |
| 7,112,223 | B2 | 9/2006 | Davis |

(56) References Cited

U.S. PATENT DOCUMENTS

| | | |
|---|---|---|
| 7,135,024 B2 | 11/2006 | Cook et al. |
| 7,135,043 B2 | 11/2006 | Nakahara et al. |
| 7,163,561 B2 | 1/2007 | Michelson |
| 7,172,627 B2 | 2/2007 | Fiere et al. |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,238,206 B2 | 7/2007 | Lange et al. |
| 7,255,698 B2 | 8/2007 | Michelson |
| 7,276,081 B1 | 10/2007 | Coates et al. |
| 7,288,094 B2 | 10/2007 | Lindemann et al. |
| 7,288,095 B2 | 10/2007 | Baynham et al. |
| 7,288,114 B2 | 10/2007 | Lange |
| 7,306,605 B2 | 12/2007 | Ross |
| 7,309,358 B2 | 12/2007 | Berry et al. |
| 7,311,734 B2 | 12/2007 | Van et al. |
| 7,316,714 B2 | 1/2008 | Gordon et al. |
| 7,318,839 B2 | 1/2008 | Malberg et al. |
| 7,323,011 B2 | 1/2008 | Shepard et al. |
| 7,326,248 B2 | 2/2008 | Michelson |
| 7,332,209 B2 | 2/2008 | Yokouchi et al. |
| 7,338,525 B2 | 3/2008 | Ferree |
| 7,341,587 B2 | 3/2008 | Molz et al. |
| 7,341,590 B2 | 3/2008 | Ferree |
| 7,354,452 B2 | 4/2008 | Foley |
| 7,361,193 B2 | 4/2008 | Frey et al. |
| 7,435,262 B2 | 10/2008 | Michelson |
| 7,438,715 B2 | 10/2008 | Doubler et al. |
| 7,442,209 B2 | 10/2008 | Michelson |
| 7,452,370 B2 | 11/2008 | Anderson |
| 7,491,237 B2 | 2/2009 | Randall et al. |
| 7,513,900 B2 | 4/2009 | Carrison et al. |
| 7,527,641 B2 | 5/2009 | Suh |
| 7,594,931 B2 | 9/2009 | Louis et al. |
| 7,594,932 B2 | 9/2009 | Aferzon et al. |
| 7,601,171 B2 | 10/2009 | Ainsworth et al. |
| 7,601,173 B2 | 10/2009 | Messerli et al. |
| 7,608,062 B2 | 10/2009 | Sweeney |
| 7,618,456 B2 | 11/2009 | Mathieu et al. |
| 7,628,816 B2 | 12/2009 | Magerl et al. |
| 7,641,665 B2 | 1/2010 | Zubok et al. |
| 7,655,042 B2 | 2/2010 | Foley et al. |
| 7,658,766 B2 | 2/2010 | Melkent et al. |
| 7,662,182 B2 | 2/2010 | Zubok et al. |
| 7,674,279 B2 | 3/2010 | Johnson |
| 7,704,255 B2 | 4/2010 | Michelson |
| 7,726,002 B2 | 6/2010 | Shimp et al. |
| 7,794,502 B2 | 9/2010 | Michelson |
| 7,815,643 B2 | 10/2010 | Johnson et al. |
| 7,815,681 B2 | 10/2010 | Ferguson |
| 7,846,206 B2 | 12/2010 | Oglaza et al. |
| 7,846,210 B2 | 12/2010 | Perez-Cruet et al. |
| 7,862,616 B2 | 1/2011 | Lechmann et al. |
| 7,871,441 B2 | 1/2011 | Eckman |
| 7,875,062 B2 | 1/2011 | Lindemann et al. |
| 7,875,076 B2 | 1/2011 | Mathieu et al. |
| 7,883,531 B2 | 2/2011 | De Coninck |
| 7,887,591 B2 | 2/2011 | Aebi et al. |
| 7,887,595 B1 | 2/2011 | Pimenta |
| 7,909,877 B2 | 3/2011 | Krueger et al. |
| 7,942,903 B2 | 5/2011 | Moskowitz et al. |
| 7,993,403 B2 | 8/2011 | Foley et al. |
| 8,002,808 B2 | 8/2011 | Morrison et al. |
| 8,007,523 B2 | 8/2011 | Wagner et al. |
| 8,187,329 B2 | 5/2012 | Theofilos |
| 8,206,423 B2 | 6/2012 | Siegal |
| 8,216,312 B2 | 7/2012 | Gray |
| 8,236,029 B2 | 8/2012 | Siegal |
| 8,241,328 B2 | 8/2012 | Siegal |
| 8,246,622 B2 | 8/2012 | Siegal et al. |
| 8,323,342 B2 | 12/2012 | Schwab |
| 8,328,812 B2 | 12/2012 | Siegal et al. |
| 8,336,559 B2 | 12/2012 | Kallabat et al. |
| 8,337,559 B2 | 12/2012 | Hansell et al. |
| 8,343,219 B2 | 1/2013 | Allain et al. |
| 8,349,015 B2 | 1/2013 | Bae et al. |
| 8,357,200 B2 | 1/2013 | Adl |
| 8,377,133 B2 | 2/2013 | Yuan et al. |
| 8,454,694 B2 | 6/2013 | Armstrong et al. |
| 8,460,385 B1 | 6/2013 | Wensel |
| 8,460,387 B2 | 6/2013 | Theofilos |
| 8,460,388 B2 | 6/2013 | Kirwan et al. |
| 8,465,524 B2 | 6/2013 | Siegal |
| 8,470,044 B2 | 6/2013 | Bertholet et al. |
| 8,480,747 B2 | 7/2013 | Melkent et al. |
| 8,486,109 B2 | 7/2013 | Siegal |
| 8,491,653 B2 | 7/2013 | Zucherman et al. |
| 8,491,658 B1 | 7/2013 | Etminan |
| 8,496,691 B2 | 7/2013 | Blain |
| 8,496,708 B2 | 7/2013 | Blain |
| 8,500,783 B2 | 8/2013 | Baynham |
| 8,551,175 B1 | 10/2013 | Wensel |
| 8,562,651 B2 | 10/2013 | Metcalf et al. |
| 8,597,330 B2 | 12/2013 | Siegal |
| 8,613,772 B2 | 12/2013 | Bray et al. |
| 8,617,245 B2 | 12/2013 | Brett |
| 8,628,578 B2 | 1/2014 | Miller et al. |
| 8,641,765 B2 | 2/2014 | Muhanna |
| 8,672,977 B2 | 3/2014 | Siegal et al. |
| 8,690,928 B1 | 4/2014 | Walkenhorst et al. |
| 8,690,948 B2 | 4/2014 | Armstrong et al. |
| 8,747,443 B2 | 6/2014 | Aferzon |
| 8,758,439 B2 | 6/2014 | Linares |
| 8,777,993 B2 | 7/2014 | Siegal et al. |
| 8,821,555 B2 | 9/2014 | Bae et al. |
| 8,845,638 B2 | 9/2014 | Siegal et al. |
| 8,900,235 B2 | 12/2014 | Siegal |
| 8,906,098 B2 | 12/2014 | Siegal |
| 8,932,358 B1 | 1/2015 | Nehls |
| 8,932,359 B2 | 1/2015 | Brett |
| 8,956,416 B2 | 2/2015 | McCarthy |
| 9,005,293 B2 | 4/2015 | Moskowitz et al. |
| 9,005,295 B2 | 4/2015 | Kueenzi et al. |
| 9,017,408 B2 | 4/2015 | Siegal et al. |
| 9,017,413 B2 | 4/2015 | Siegal et al. |
| 9,039,768 B2 | 5/2015 | Voellmicke |
| 9,044,334 B2 | 6/2015 | Siegal et al. |
| 9,138,330 B2 | 9/2015 | Hansell et al. |
| 9,192,419 B2 | 11/2015 | McDonough et al. |
| 9,248,028 B2 | 2/2016 | Gamache |
| 9,254,138 B2 | 2/2016 | Siegal et al. |
| 9,265,546 B2 | 2/2016 | Blain |
| 9,265,621 B2 | 2/2016 | Voellmicke |
| 9,271,836 B2 | 3/2016 | Pavento et al. |
| 9,278,009 B2 | 3/2016 | Bray et al. |
| 9,283,091 B2 | 3/2016 | Melkent et al. |
| 9,283,092 B2 | 3/2016 | Siegal et al. |
| 9,289,311 B1 | 3/2016 | Whipple |
| 9,364,272 B2 | 6/2016 | Binder et al. |
| 9,402,735 B2 * | 8/2016 | McDonough ......... A61F 2/4455 |
| 9,402,738 B2 | 8/2016 | Niemiec et al. |
| 9,408,712 B2 | 8/2016 | Siegal et al. |
| 9,445,918 B1 | 9/2016 | Lin et al. |
| 9,492,286 B2 | 11/2016 | Biedermann et al. |
| 9,566,165 B2 | 2/2017 | Lee et al. |
| 9,592,129 B2 | 3/2017 | Slivka et al. |
| 9,662,225 B2 | 5/2017 | Pavento et al. |
| 9,668,877 B2 | 6/2017 | Pavento et al. |
| 9,848,992 B2 | 12/2017 | McDonough et al. |
| 9,867,718 B2 | 1/2018 | Schmura et al. |
| 9,872,781 B2 | 1/2018 | Hawkins et al. |
| 9,987,142 B2 | 6/2018 | McConnell |
| 10,327,915 B2 | 6/2019 | Pavento et al. |
| 2001/0016775 A1 | 8/2001 | Scarborough et al. |
| 2001/0031968 A1 | 10/2001 | Dorchak et al. |
| 2001/0032020 A1 | 10/2001 | Besselink |
| 2002/0029044 A1 | 3/2002 | Monassevitch et al. |
| 2002/0029082 A1 | 3/2002 | Muhanna |
| 2002/0082693 A1 | 6/2002 | Ahlgren |
| 2002/0095155 A1 | 7/2002 | Michelson |
| 2002/0099376 A1 | 7/2002 | Michelson |
| 2002/0138146 A1 | 9/2002 | Jackson |
| 2002/0143328 A1 | 10/2002 | Shluzas et al. |

(56) References Cited

U.S. PATENT DOCUMENTS

| | | |
|---|---|---|
| 2002/0151976 A1 | 10/2002 | Foley et al. |
| 2002/0156475 A1 | 10/2002 | Lerch et al. |
| 2003/0004576 A1 | 1/2003 | Thalgott |
| 2003/0014113 A1 | 1/2003 | Ralph et al. |
| 2003/0028197 A1 | 2/2003 | Hanson et al. |
| 2003/0045940 A1 | 3/2003 | Eberlein et al. |
| 2003/0050645 A1 | 3/2003 | Parker et al. |
| 2003/0083748 A1 | 5/2003 | Lee et al. |
| 2003/0100949 A1 | 5/2003 | Michelson |
| 2003/0125739 A1 | 7/2003 | Bagga et al. |
| 2003/0130739 A1 | 7/2003 | Gerbec et al. |
| 2003/0153975 A1 | 8/2003 | Byrd et al. |
| 2003/0158555 A1 | 8/2003 | Sanders et al. |
| 2003/0187440 A1 | 10/2003 | Richelsoph et al. |
| 2003/0187506 A1 | 10/2003 | Ross et al. |
| 2003/0195632 A1 | 10/2003 | Foley et al. |
| 2003/0208203 A1 | 11/2003 | Lim et al. |
| 2003/0225409 A1 | 12/2003 | Freid et al. |
| 2004/0024464 A1 | 2/2004 | Errico et al. |
| 2004/0034430 A1 | 2/2004 | Falahee |
| 2004/0073213 A1 | 4/2004 | Serhan et al. |
| 2004/0088055 A1 | 5/2004 | Hanson et al. |
| 2004/0092929 A1 | 5/2004 | Zindrick |
| 2004/0106996 A1 | 6/2004 | Liu et al. |
| 2004/0111089 A1 | 6/2004 | Stevens et al. |
| 2004/0117022 A1 | 6/2004 | Marnay et al. |
| 2004/0127902 A1 | 7/2004 | Suzuki et al. |
| 2004/0127990 A1 | 7/2004 | Bartish et al. |
| 2004/0138662 A1 | 7/2004 | Landry et al. |
| 2004/0153065 A1 | 8/2004 | Lim |
| 2004/0153072 A1 | 8/2004 | Bonutti |
| 2004/0162618 A1 | 8/2004 | Mujwid et al. |
| 2004/0167625 A1 | 8/2004 | Beyar et al. |
| 2004/0193269 A1 | 9/2004 | Fraser et al. |
| 2004/0193271 A1 | 9/2004 | Fraser et al. |
| 2004/0199253 A1 | 10/2004 | Link et al. |
| 2004/0199254 A1 | 10/2004 | Louis et al. |
| 2004/0210219 A1 | 10/2004 | Bray |
| 2004/0230309 A1 | 11/2004 | Dimauro et al. |
| 2004/0249377 A1 | 12/2004 | Kaes et al. |
| 2004/0254644 A1 | 12/2004 | Taylor |
| 2004/0260286 A1 | 12/2004 | Ferree |
| 2005/0015147 A1 | 1/2005 | Schwardt et al. |
| 2005/0021144 A1 | 1/2005 | Malberg et al. |
| 2005/0033433 A1 | 2/2005 | Michelson |
| 2005/0038513 A1 | 2/2005 | Michelson |
| 2005/0043800 A1 | 2/2005 | Paul et al. |
| 2005/0060034 A1 | 3/2005 | Berry et al. |
| 2005/0065608 A1 | 3/2005 | Michelson |
| 2005/0071006 A1 | 3/2005 | Kirschman |
| 2005/0071008 A1 | 3/2005 | Kirschman |
| 2005/0085913 A1 | 4/2005 | Fraser et al. |
| 2005/0096657 A1 | 5/2005 | Autericque et al. |
| 2005/0101960 A1 | 5/2005 | Fiere et al. |
| 2005/0113920 A1 | 5/2005 | Foley et al. |
| 2005/0143749 A1 | 6/2005 | Zalenski et al. |
| 2005/0143827 A1 | 6/2005 | Globerman et al. |
| 2005/0149192 A1 | 7/2005 | Zucherman et al. |
| 2005/0149193 A1 | 7/2005 | Zucherman et al. |
| 2005/0154391 A1 | 7/2005 | Doherty et al. |
| 2005/0159813 A1 | 7/2005 | Molz, IV |
| 2005/0159819 A1 | 7/2005 | McCormack et al. |
| 2005/0165483 A1 | 7/2005 | Ray et al. |
| 2005/0177240 A1 | 8/2005 | Blain |
| 2005/0177245 A1 | 8/2005 | Leatherbury et al. |
| 2005/0182416 A1 | 8/2005 | Lim et al. |
| 2005/0203515 A1 | 9/2005 | Doherty et al. |
| 2005/0209696 A1 | 9/2005 | Lin et al. |
| 2005/0216081 A1 | 9/2005 | Taylor |
| 2005/0251260 A1 | 11/2005 | Gerber et al. |
| 2005/0261768 A1 | 11/2005 | Trieu |
| 2005/0277938 A1 | 12/2005 | Parsons |
| 2005/0278036 A1 | 12/2005 | Leonard et al. |
| 2006/0025860 A1 | 2/2006 | Li |
| 2006/0030851 A1 | 2/2006 | Bray et al. |
| 2006/0036261 A1 | 2/2006 | McDonnell |
| 2006/0058801 A1 | 3/2006 | Schlienger et al. |
| 2006/0079961 A1 | 4/2006 | Michelson |
| 2006/0085071 A1 | 4/2006 | Lechmann et al. |
| 2006/0129424 A1 | 6/2006 | Chan |
| 2006/0136063 A1 | 6/2006 | Zeegers |
| 2006/0142765 A9 | 6/2006 | Dixon et al. |
| 2006/0142858 A1 | 6/2006 | Colleran et al. |
| 2006/0142863 A1 | 6/2006 | Fraser et al. |
| 2006/0152863 A1 | 7/2006 | Freitag et al. |
| 2006/0178745 A1 | 8/2006 | Bartish et al. |
| 2006/0190083 A1 | 8/2006 | Arnin et al. |
| 2006/0211952 A1 | 9/2006 | Kennedy, II |
| 2006/0229609 A1 | 10/2006 | Wang |
| 2006/0229724 A1 | 10/2006 | Lechmann et al. |
| 2006/0229729 A1 | 10/2006 | Gordon et al. |
| 2006/0235403 A1 | 10/2006 | Blain |
| 2006/0235409 A1 | 10/2006 | Blain |
| 2006/0235411 A1 | 10/2006 | Blain et al. |
| 2006/0235518 A1 | 10/2006 | Blain |
| 2006/0235535 A1 | 10/2006 | Ferree et al. |
| 2006/0241597 A1 | 10/2006 | Mitchell et al. |
| 2006/0241761 A1 | 10/2006 | Gately |
| 2006/0247650 A1 | 11/2006 | Yerby et al. |
| 2006/0259147 A1 | 11/2006 | Krishna et al. |
| 2006/0265068 A1 | 11/2006 | Schwab |
| 2006/0293753 A1 | 12/2006 | Thramann |
| 2007/0049941 A1 | 3/2007 | Thramann |
| 2007/0055252 A1 | 3/2007 | Blain et al. |
| 2007/0067035 A1 | 3/2007 | Falahee |
| 2007/0073398 A1 | 3/2007 | Fabian et al. |
| 2007/0106384 A1 | 5/2007 | Bray et al. |
| 2007/0106388 A1 | 5/2007 | Michelson |
| 2007/0129804 A1 | 6/2007 | Bentley et al. |
| 2007/0149978 A1 | 6/2007 | Shezifi et al. |
| 2007/0162138 A1 | 7/2007 | Heinz |
| 2007/0198016 A1 | 8/2007 | Zang et al. |
| 2007/0213737 A1 | 9/2007 | Schermerhorn et al. |
| 2007/0213820 A1 | 9/2007 | Magerl et al. |
| 2007/0219635 A1 | 9/2007 | Mathieu et al. |
| 2007/0233118 A1 | 10/2007 | McLain |
| 2007/0233253 A1 | 10/2007 | Bray et al. |
| 2007/0233254 A1 | 10/2007 | Grotz et al. |
| 2007/0233261 A1 | 10/2007 | Lopez et al. |
| 2007/0233263 A1 | 10/2007 | Melkent et al. |
| 2007/0239278 A1 | 10/2007 | Heinz |
| 2007/0250167 A1 | 10/2007 | Bray et al. |
| 2007/0255416 A1 | 11/2007 | Melkent et al. |
| 2007/0265631 A1 | 11/2007 | Fox |
| 2007/0270957 A1 | 11/2007 | Heinz |
| 2007/0270965 A1 | 11/2007 | Ferguson |
| 2007/0276490 A1 | 11/2007 | Mateyka |
| 2007/0282443 A1 | 12/2007 | Globerman et al. |
| 2007/0282449 A1 | 12/2007 | De et al. |
| 2007/0293948 A1 | 12/2007 | Bagga et al. |
| 2007/0299521 A1 | 12/2007 | Glenn et al. |
| 2008/0015694 A1 | 1/2008 | Tribus |
| 2008/0015701 A1 | 1/2008 | Garcia et al. |
| 2008/0021476 A1 | 1/2008 | Kirschman |
| 2008/0027550 A1 | 1/2008 | Link et al. |
| 2008/0033440 A1 | 2/2008 | Moskowitz et al. |
| 2008/0033480 A1 | 2/2008 | Hardert |
| 2008/0051890 A1 | 2/2008 | Waugh et al. |
| 2008/0051897 A1 | 2/2008 | Lopez et al. |
| 2008/0065219 A1 | 3/2008 | Dye |
| 2008/0077247 A1 | 3/2008 | Murillo et al. |
| 2008/0082173 A1 | 4/2008 | Delurio et al. |
| 2008/0097436 A1 | 4/2008 | Culbert et al. |
| 2008/0103597 A1 | 5/2008 | Lechmann et al. |
| 2008/0103598 A1 | 5/2008 | Trudeau et al. |
| 2008/0109005 A1 | 5/2008 | Trudeau et al. |
| 2008/0125865 A1 | 5/2008 | Abdelgany |
| 2008/0132949 A1 | 6/2008 | Aferzon et al. |
| 2008/0132958 A1 | 6/2008 | Pech et al. |
| 2008/0133012 A1 | 6/2008 | McGuckin |
| 2008/0133014 A1 | 6/2008 | Gately et al. |
| 2008/0140085 A1* | 6/2008 | Gately ............ A61F 2/4465 606/99 |
| 2008/0154379 A1 | 6/2008 | Steiner et al. |

(56) References Cited

U.S. PATENT DOCUMENTS

| | | |
|---|---|---|
| 2008/0161922 A1 | 7/2008 | Rhoda |
| 2008/0161925 A1 | 7/2008 | Brittan et al. |
| 2008/0167666 A1 | 7/2008 | Fiere et al. |
| 2008/0177307 A1 | 7/2008 | Moskowitz et al. |
| 2008/0183293 A1 | 7/2008 | Parry et al. |
| 2008/0183294 A1 | 7/2008 | Adl |
| 2008/0221690 A1 | 9/2008 | Chaput et al. |
| 2008/0221694 A1* | 9/2008 | Warnick ............... A61F 2/4611 623/17.16 |
| 2008/0234822 A1 | 9/2008 | Govil et al. |
| 2008/0243136 A1 | 10/2008 | Prager et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0255620 A1 | 10/2008 | Strauss et al. |
| 2008/0269806 A1 | 10/2008 | Zhang et al. |
| 2008/0281425 A1 | 11/2008 | Thalgott et al. |
| 2008/0294262 A1 | 11/2008 | Levieux |
| 2008/0300601 A1 | 12/2008 | Fabian et al. |
| 2008/0300634 A1 | 12/2008 | Gray |
| 2008/0306596 A1 | 12/2008 | Jones et al. |
| 2008/0306598 A1 | 12/2008 | Hansen et al. |
| 2008/0312698 A1 | 12/2008 | Bergeron et al. |
| 2008/0312742 A1 | 12/2008 | Abernathie |
| 2008/0312743 A1 | 12/2008 | Vila et al. |
| 2009/0012529 A1 | 1/2009 | Blain et al. |
| 2009/0030421 A1 | 1/2009 | Hawkins et al. |
| 2009/0030519 A1 | 1/2009 | Falahee |
| 2009/0030520 A1 | 1/2009 | Biedermann et al. |
| 2009/0062921 A1 | 3/2009 | Michelson |
| 2009/0069895 A1 | 3/2009 | Gittings et al. |
| 2009/0088849 A1 | 4/2009 | Armstrong et al. |
| 2009/0099554 A1 | 4/2009 | Forster et al. |
| 2009/0099610 A1 | 4/2009 | Johnson et al. |
| 2009/0099661 A1 | 4/2009 | Bhattacharya et al. |
| 2009/0105771 A1 | 4/2009 | Lei et al. |
| 2009/0105774 A1 | 4/2009 | Jones et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0125028 A1 | 5/2009 | Teisen et al. |
| 2009/0131988 A1 | 5/2009 | Bush et al. |
| 2009/0132054 A1 | 5/2009 | Zeegers |
| 2009/0143859 A1 | 6/2009 | McClellan et al. |
| 2009/0164020 A1 | 6/2009 | Janowski et al. |
| 2009/0182428 A1 | 7/2009 | McClellan et al. |
| 2009/0182430 A1 | 7/2009 | Tyber et al. |
| 2009/0192549 A1 | 7/2009 | Sanders et al. |
| 2009/0192613 A1 | 7/2009 | Wing et al. |
| 2009/0192615 A1 | 7/2009 | Tyber et al. |
| 2009/0192616 A1 | 7/2009 | Zielinski |
| 2009/0198245 A1 | 8/2009 | Phan |
| 2009/0198287 A1 | 8/2009 | Chiu |
| 2009/0198339 A1 | 8/2009 | Kleiner et al. |
| 2009/0210062 A1 | 8/2009 | Thalgott et al. |
| 2009/0210064 A1 | 8/2009 | Lechmann et al. |
| 2009/0224023 A1 | 9/2009 | Moskowitz et al. |
| 2009/0234364 A1 | 9/2009 | Crook |
| 2009/0240333 A1 | 9/2009 | Trudeau et al. |
| 2009/0248092 A1 | 10/2009 | Bellas et al. |
| 2009/0259316 A1 | 10/2009 | Ginn et al. |
| 2009/0265007 A1 | 10/2009 | Colleran |
| 2009/0270873 A1 | 10/2009 | Fabian |
| 2009/0287251 A1 | 11/2009 | Bae et al. |
| 2009/0306779 A1 | 12/2009 | Ahn |
| 2009/0326543 A1 | 12/2009 | Fabian, Jr. |
| 2009/0326580 A1 | 12/2009 | Anderson et al. |
| 2009/0326589 A1 | 12/2009 | Lemoine et al. |
| 2010/0004747 A1 | 1/2010 | Lin |
| 2010/0016901 A1 | 1/2010 | Robinson |
| 2010/0016973 A1 | 1/2010 | De et al. |
| 2010/0023128 A1 | 1/2010 | Malberg |
| 2010/0024779 A1 | 2/2010 | Makita |
| 2010/0030334 A1 | 2/2010 | Molz, IV |
| 2010/0036496 A1 | 2/2010 | Yu et al. |
| 2010/0042159 A1 | 2/2010 | Butler |
| 2010/0057206 A1 | 3/2010 | Duffield et al. |
| 2010/0069969 A1 | 3/2010 | Ampuero et al. |
| 2010/0070036 A1 | 3/2010 | Implicito |
| 2010/0070037 A1 | 3/2010 | Parry et al. |
| 2010/0087925 A1 | 4/2010 | Kostuik et al. |
| 2010/0106249 A1 | 4/2010 | Tyber et al. |
| 2010/0125334 A1 | 5/2010 | Krueger |
| 2010/0137987 A1 | 6/2010 | Diao et al. |
| 2010/0145457 A1 | 6/2010 | Felt et al. |
| 2010/0145459 A1 | 6/2010 | McDonough et al. |
| 2010/0145460 A1 | 6/2010 | McDonough et al. |
| 2010/0179656 A1 | 7/2010 | Theofilos |
| 2010/0185287 A1 | 7/2010 | Allard et al. |
| 2010/0185289 A1 | 7/2010 | Kirwan et al. |
| 2010/0185292 A1 | 7/2010 | Hochschuler et al. |
| 2010/0191334 A1 | 7/2010 | Keller |
| 2010/0204739 A1 | 8/2010 | Bae et al. |
| 2010/0217325 A1 | 8/2010 | Hochschuler et al. |
| 2010/0217393 A1 | 8/2010 | Theofilos |
| 2010/0241231 A1 | 9/2010 | Marino et al. |
| 2010/0249935 A1 | 9/2010 | Slivka et al. |
| 2010/0249937 A1 | 9/2010 | Blain et al. |
| 2010/0256759 A1* | 10/2010 | Hansell ............... A61F 2/4611 623/17.11 |
| 2010/0256760 A1* | 10/2010 | Hansell ............... A61F 2/4611 623/17.11 |
| 2010/0268338 A1 | 10/2010 | Melkent et al. |
| 2010/0286777 A1 | 11/2010 | Errico et al. |
| 2010/0286781 A1 | 11/2010 | Bullard |
| 2010/0286783 A1 | 11/2010 | Lechmann et al. |
| 2010/0292696 A1 | 11/2010 | Chantelot et al. |
| 2010/0292737 A1 | 11/2010 | Suh |
| 2010/0305704 A1 | 12/2010 | Messerli et al. |
| 2010/0312345 A1 | 12/2010 | Duffield et al. |
| 2010/0312346 A1 | 12/2010 | Kueenzi et al. |
| 2010/0324683 A1 | 12/2010 | Reichen et al. |
| 2011/0009908 A1 | 1/2011 | Ferguson |
| 2011/0009966 A1 | 1/2011 | Michelson |
| 2011/0015675 A1 | 1/2011 | Howard et al. |
| 2011/0015745 A1 | 1/2011 | Bucci |
| 2011/0082550 A1 | 4/2011 | Yeh |
| 2011/0082555 A1 | 4/2011 | Martz et al. |
| 2011/0098747 A1 | 4/2011 | Donner et al. |
| 2011/0106159 A1 | 5/2011 | Nazeck |
| 2011/0118840 A1 | 5/2011 | Huntsman et al. |
| 2011/0144703 A1 | 6/2011 | Krause et al. |
| 2011/0160866 A1 | 6/2011 | Laurence et al. |
| 2011/0166656 A1 | 7/2011 | Thalgott et al. |
| 2011/0184415 A1 | 7/2011 | Anderson et al. |
| 2011/0185292 A1 | 7/2011 | Chawla et al. |
| 2011/0190892 A1 | 8/2011 | Kirschman |
| 2011/0202136 A1 | 8/2011 | Brittan et al. |
| 2011/0208311 A1 | 8/2011 | Janowski |
| 2011/0213421 A1 | 9/2011 | Binder et al. |
| 2011/0230970 A1* | 9/2011 | Lynn ................... A61F 2/4611 623/17.16 |
| 2011/0230971 A1 | 9/2011 | Donner et al. |
| 2011/0251689 A1 | 10/2011 | Seifert et al. |
| 2011/0276142 A1* | 11/2011 | Niemiec ............... A61F 2/4425 623/17.16 |
| 2011/0282453 A1 | 11/2011 | Greenhalgh et al. |
| 2011/0319896 A1 | 12/2011 | Papenfuss et al. |
| 2011/0319898 A1 | 12/2011 | O'Neil et al. |
| 2011/0319943 A1 | 12/2011 | Donahoe et al. |
| 2011/0319998 A1 | 12/2011 | O'Neil et al. |
| 2012/0041559 A1 | 2/2012 | Melkent et al. |
| 2012/0078371 A1 | 3/2012 | Gamache et al. |
| 2012/0078372 A1 | 3/2012 | Gamache et al. |
| 2012/0078373 A1* | 3/2012 | Gamache ............. A61F 2/4455 623/17.16 |
| 2012/0083887 A1 | 4/2012 | Purcell et al. |
| 2012/0083889 A1 | 4/2012 | Purcell et al. |
| 2012/0143336 A1* | 6/2012 | Aflatoon ............. A61F 2/4465 623/17.16 |
| 2012/0150301 A1 | 6/2012 | Gamache et al. |
| 2012/0150303 A1 | 6/2012 | Linares |
| 2012/0158143 A1 | 6/2012 | Shapiro |
| 2012/0191190 A1 | 7/2012 | Trieu |

(56) References Cited

U.S. PATENT DOCUMENTS

| | | |
|---|---|---|
| 2012/0191204 A1 | 7/2012 | Bae et al. |
| 2012/0197401 A1 | 8/2012 | Duncan et al. |
| 2012/0203230 A1 | 8/2012 | Adams |
| 2012/0209331 A1 | 8/2012 | Michelson |
| 2012/0215315 A1 | 8/2012 | Hochschuler et al. |
| 2012/0226319 A1 | 9/2012 | Armstrong et al. |
| 2012/0253406 A1 | 10/2012 | Bae et al. |
| 2013/0041471 A1 | 2/2013 | Siegal et al. |
| 2013/0060337 A1 | 3/2013 | Petersheim et al. |
| 2013/0073044 A1 | 3/2013 | Gamache |
| 2013/0079883 A1 | 3/2013 | Butler et al. |
| 2013/0103102 A1* | 4/2013 | Taylor ............ A61F 2/4611 606/86 A |
| 2013/0144391 A1 | 6/2013 | Siegal et al. |
| 2013/0166027 A1 | 6/2013 | Bellas |
| 2013/0238095 A1 | 9/2013 | Pavento et al. |
| 2013/0261747 A1 | 10/2013 | Geisert |
| 2013/0268080 A1 | 10/2013 | Melkent et al. |
| 2013/0310939 A1 | 11/2013 | Fabian et al. |
| 2013/0325071 A1 | 12/2013 | Niemiec et al. |
| 2013/0345813 A1 | 12/2013 | Frank et al. |
| 2014/0039623 A1 | 2/2014 | Iott et al. |
| 2014/0067069 A1 | 3/2014 | Lopez |
| 2014/0094916 A1 | 4/2014 | Glerum et al. |
| 2014/0107786 A1 | 4/2014 | Geisler et al. |
| 2014/0114415 A1 | 4/2014 | Tyber |
| 2014/0121774 A1 | 5/2014 | Glerum et al. |
| 2014/0135930 A1 | 5/2014 | Georges |
| 2014/0142705 A1 | 5/2014 | Duffield et al. |
| 2014/0156009 A1 | 6/2014 | Armstrong et al. |
| 2014/0172103 A1 | 6/2014 | O'Neil et al. |
| 2014/0336771 A1 | 11/2014 | Zambiasi et al. |
| 2014/0364917 A1 | 12/2014 | Sandstrom et al. |
| 2015/0230929 A1 | 8/2015 | Lorio |
| 2015/0297356 A1 | 10/2015 | Gamache et al. |
| 2015/0313721 A1 | 11/2015 | Gamache et al. |
| 2015/0374511 A1 | 12/2015 | Pavento et al. |
| 2016/0045325 A1 | 2/2016 | Bellas et al. |
| 2016/0067052 A1 | 3/2016 | Cain |
| 2016/0128846 A1 | 5/2016 | Voellmicke |
| 2016/0213487 A1 | 7/2016 | Wilson et al. |
| 2016/0317317 A1 | 11/2016 | Marchek et al. |
| 2016/0324660 A1 | 11/2016 | Pavento et al. |
| 2016/0324662 A1 | 11/2016 | McDonough et al. |
| 2017/0065427 A1 | 3/2017 | Songer |
| 2017/0095341 A1 | 4/2017 | Smith |
| 2017/0304068 A1 | 10/2017 | Bellas et al. |
| 2017/0312090 A1 | 11/2017 | Sharabani et al. |
| 2020/0008958 A1 | 1/2020 | Gamache et al. |

FOREIGN PATENT DOCUMENTS

| | | |
|---|---|---|
| DE | 19710392 C1 | 7/1999 |
| EP | 1121906 A2 | 8/2001 |
| EP | 1609444 A1 | 12/2005 |
| EP | 1683490 A2 | 7/2006 |
| EP | 1774926 A2 | 4/2007 |
| EP | 1459711 B1 | 7/2007 |
| EP | 1847240 A1 | 10/2007 |
| EP | 1506753 B1 | 9/2009 |
| EP | 2156812 A1 | 2/2010 |
| FR | 2634260 A1 | 1/1990 |
| FR | 2894130 A1 | 6/2007 |
| GB | 0457673 A | 12/1936 |
| GB | 2220729 A | 1/1990 |
| GB | 2457673 A | 8/2009 |
| JP | 2005-524472 A | 8/2005 |
| JP | 2006-524114 A | 10/2006 |
| JP | 2007-516808 | 6/2007 |
| JP | 2008-514362 A | 5/2008 |
| JP | 2012-508044 | 4/2012 |
| JP | 2013-516206 A | 5/2013 |
| WO | 98/04217 A1 | 2/1998 |
| WO | 98/34568 A1 | 8/1998 |
| WO | 99/38463 A2 | 8/1999 |
| WO | 99/52473 A1 | 10/1999 |
| WO | 01/08864 A1 | 2/2001 |
| WO | 02/13732 A2 | 2/2002 |
| WO | 03/05938 A1 | 1/2003 |
| WO | 03/05939 | 1/2003 |
| WO | 2003/003951 A1 | 1/2003 |
| WO | 03/47473 A2 | 6/2003 |
| WO | 03/70128 A1 | 8/2003 |
| WO | 03/90650 A1 | 11/2003 |
| WO | 2004/069106 A1 | 8/2004 |
| WO | 2005/020861 A1 | 3/2005 |
| WO | 2006/058281 A2 | 6/2006 |
| WO | 2006/084057 A1 | 8/2006 |
| WO | 2007/003785 A1 | 1/2007 |
| WO | 2007/098288 A2 | 8/2007 |
| WO | 2007/118856 A1 | 10/2007 |
| WO | 2008/149223 A2 | 12/2008 |
| WO | 2009/025841 A1 | 2/2009 |
| WO | 2009/064644 A1 | 5/2009 |
| WO | 2009/091775 A2 | 7/2009 |
| WO | 2009/136009 A1 | 11/2009 |
| WO | 2010/028045 A1 | 3/2010 |
| WO | 2010/033786 A2 | 3/2010 |
| WO | 2010/054181 A1 | 5/2010 |
| WO | 2010/054208 A1 | 5/2010 |
| WO | 2010/092893 A1 | 8/2010 |
| WO | 2010/099239 A2 | 9/2010 |
| WO | 2010/121028 A2 | 10/2010 |
| WO | 2010/125514 A1 | 11/2010 |
| WO | 2011/008864 A1 | 1/2011 |
| WO | 2011/035126 A1 | 3/2011 |
| WO | 2011/080535 A1 | 7/2011 |
| WO | 2012/047712 | 4/2012 |
| WO | 2012/056119 A1 | 5/2012 |
| WO | 2013/018062 A1 | 2/2013 |
| WO | 2013/062716 A1 | 5/2013 |
| WO | 2013/096192 A1 | 6/2013 |
| WO | 2013/191979 A1 | 12/2013 |

OTHER PUBLICATIONS

U.S. Appl. No. 13/673,061, filed Nov. 6, 2012, entitled Interbody Device With Opening to Allow Packing Graft and Other Biologics.

Search Report dated Jan. 20, 2012 for EP07855287.

Schmiedberg, "Isolation and characterization of metallic wear debris from a dynamic intervertebral disc prosthesis", J. Biomed. Mater. Res., vol. 28, Issue 11, 1277-1288, Nov. 1994.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Pederson, "Thermal Assembly of a Biomimetic Mineral/Collagen Composite", Biomaterials, 2003, vol. 2, pp. 4881-4890, Elsevier.

PCT Written Opinion of the International Searching Authority, International Application No. PCT/US2013/029026, dated May 23, 2013, 9 pages.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Kemnitzer et al., "Degradable Polymers Derived From the Amino Acid L-Tyrozine", The Handbook of Biodegradable Polymers, edited by Domb, et al., Hardwood Academic Press, 1997, pp. 251-272.

Kandziora", Biomechanical Comparison of Cervical Spine Interbody Fusion Cages", Spine, vol. 26, No. 17, pp. 1850-1857, 2001, Lippincott Williams & Wilkins, Inc.

Humphries, "Anterior Fusion of the Lumbar Spine Using an Internal Fixative Device", Surgical Forum, vol. IX, pp. 770-773, American College of Surgeons, 1959, Chicago Illinois.

(56) References Cited

OTHER PUBLICATIONS

Heller in Handbook of Biodegradable Polymers, edited by Domb, et al, Hardwood Academic Press, pp. 99-118 (1997).
Gercek, "Subsidence of Stand-Alone Cervical Cages in Anterior Interbody Fusion: Warning", Eur. Spine Journal, vol. 12, pp. 513-516, 2003, Springer-Verlag.
European Examination Report dated Mar. 19, 2014 for EP07855287.4.
Cohn, "Polymer Preprints", ACS Division of Polymer Chemistry, vol. 30(1), 1989, p. 498, (e.g. PEO/PLA).
Cohn et al., Biodegradable PEO/PLA block copolymers, Journal of Biomaterials Research, vol. 22, pp. 993-1009, 1988.
Cain, "New Stand-Alone Anterior Lumbar Inerbody Fusion Device: Bioemechanical Comparison with Established Fixation Techniques", Spine, vol. 30, No. 23, pp. 2631-2636, 2005, Lippincott Williams & Wilkins, Inc.
Allcock, "Polyphosphazenes", The Encyclopedia of Polymer Science, vol. 13, pp. 31-41, Wiley Intersciences, John Wiley & Sons, (1988).

\* cited by examiner

INTERBODY DEVICE WITH OPENING TO ALLOW PACKING GRAFT AND OTHER BIOLOGICS

CROSS-REFERENCE TO RELATED APPLICATIONS

This is a continuation application of U.S. patent application Ser. No. 13/673,061 filed Nov. 9, 2012, the disclosure of which is hereby incorporated by reference as if set forth in its entirety herein.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1$\beta$ and TNF-$\alpha$ as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the abovementioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

U.S. Pat. No. 6,432,106 (Fraser) discloses a fusion cage having an anterior threaded insertion hole and a face plate that covers this hole. The cavity of the Fraser cage comprises three vertical throughholes, with only the central vertical throughhole connecting to the anterior insertion hole.

SUMMARY OF THE INVENTION

The present invention relates to an intervertebral fusion device having a cage having an opening or window in its front wall that allows for the insertion of bone graft therethrough after the cage has been placed into the disc space. Because the cage has a single vertical through hole that connects to that window, graft may be placed through the window so as to fill the entire cavity of the cage. The device further has a faceplate that covers the front wall of the cage, thereby covering the window after the graft has been inserted. The function of the faceplate is to provide a template for screwholes that allow the cage to be securely fixed to the vertebral body.

Therefore, the present invention is advantageous in that it allows not only the insertion of bone graft (through the window) after implant placement, it also allows for its securement to adjacent vertebral bodies (via screws that pass through the faceplate).

Therefore, in accordance with the present invention, there is provided an intervertebral fusion device comprising;
  a) a cage comprising a front wall having a first window therethrough, a back wall, and two side walls connecting the front and back walls, the front wall extending continuously between the two side walls, the four walls defining a perimeter and a single vertical throughhole, and
  b) a face plate received in the window and substantially covering the first window.
    Also in accordance with the present invention, there is provided a method comprising:
    a) implanting the cage of the present invention into an intervertebral disc space,
    b) inserting bone graft material through the first window of the implanted cage and into the vertical throughhole of the cage, and
    c) inserting a face plate into the window of the front wall of the implanted cage to substantially cover the first window of the cage.

DESCRIPTION OF THE FIGURES

FIG. 2B shows an exploded version of FIG. 2a.

DETAILED DESCRIPTION OF THE INVENTION

For the purpose of the present invention, a "front wall" includes a strur connecting the two side walls, but does not include the front faces of two unconnected sidewalls.

Figure 1A:
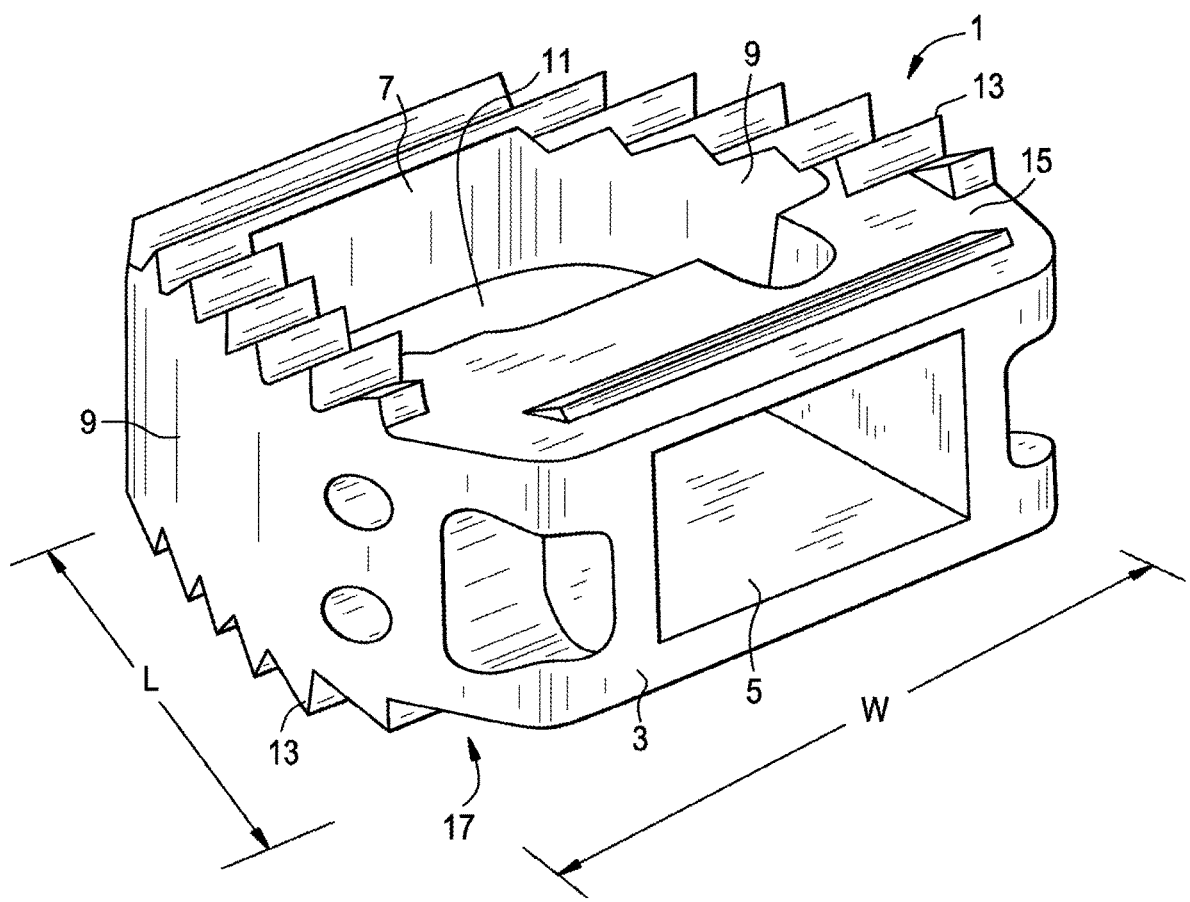
FIG. 1A discloses a cage of the present invention without a faceplate.
Figure 1B:
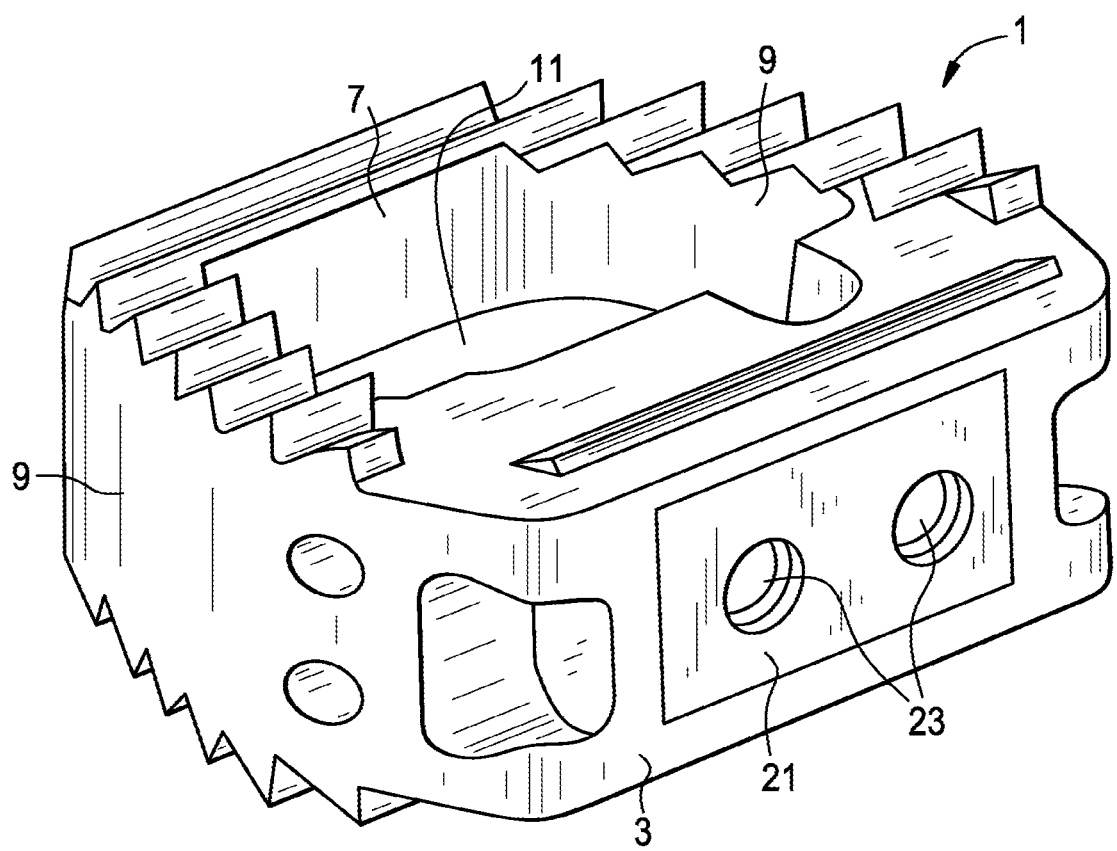
FIG. 1B shows the cage of FIG. 1a having a faceplate attached thereto.
Figure 1C:
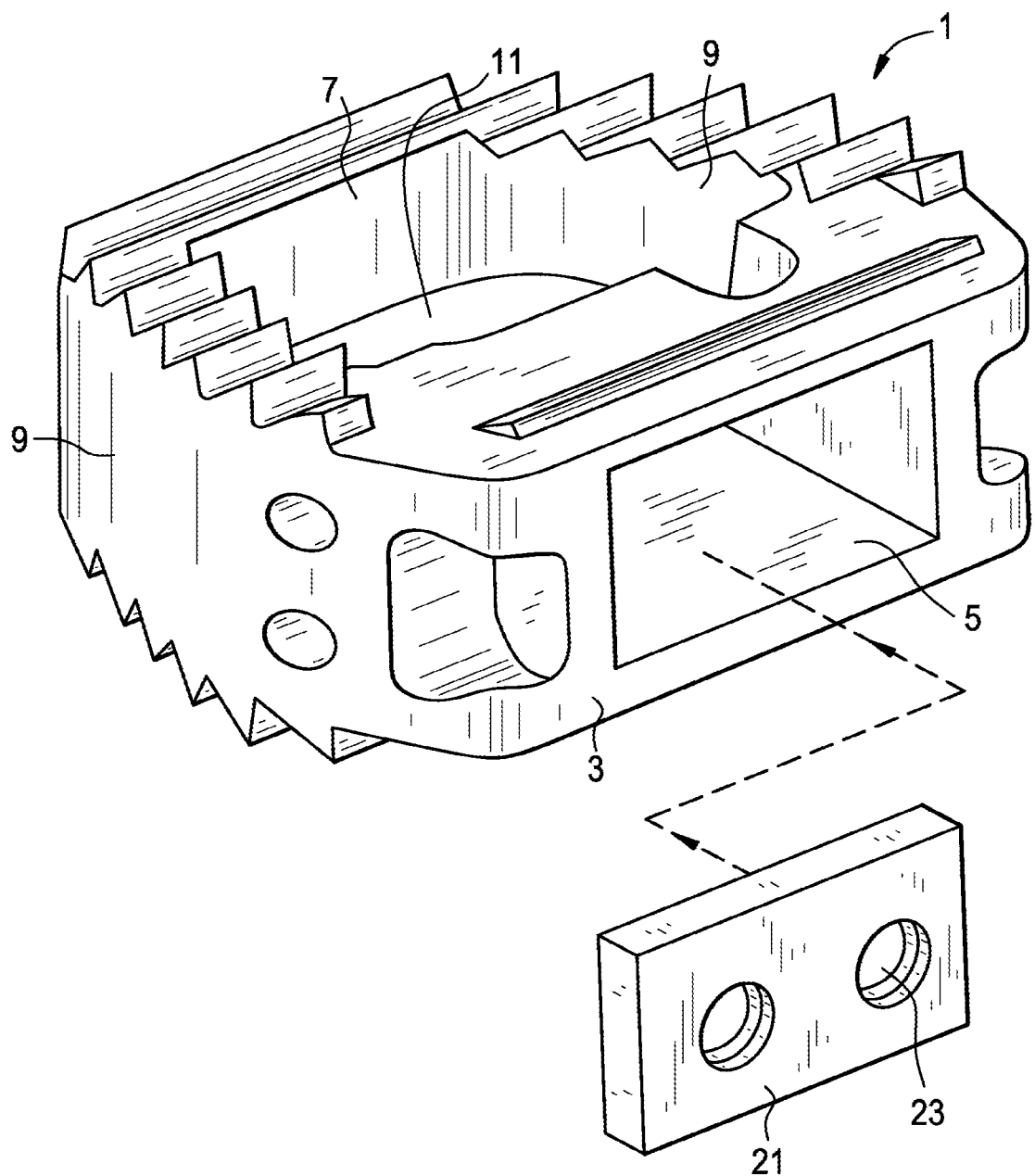
FIG. 1C discloses an exploded version of FIG. 1b.

Now referring to FIGS. 1A-1C, there is provided an intervertebral fusion device comprising;
   a) a cage 1 comprising a front wall 3 having a first window 5 therethrough, a back wall 7, and two side walls 9 connecting the front and back walls, the front wall extending continuously between the two side walls, the four walls defining a perimeter and a single vertical throughhole 11, and
   b) a face plate 21 received in the window, attached to the front wall and substantially covering the first window.

FIG. 1A shows the cage without a faceplate. In this condition, graft material can be packed or injected through the window. FIG. 1B shows the combination of the cage having a faceplate attached therethrough. Bone screws (not shown) may be received in the pair of screwholes 23 of the faceplate in order to secure the device to the adjacent vertebral bodies, thereby preventing migration.

The device of the present invention can be suited for insertion into the cervical, thoracic or lumbar disc space. The particular device shown in FIG. 1A is best suited for insertion into the cervical disc space through an anterior approach. The perimeter of the cage of FIG. 1A substantially has the shape of a cervical disc space. In some embodiments, the cervical cage has a length (L) and width (W) such that the length is between about 50% and 150% of the width, more preferably between about 80% and 120% of the width. Preferably, the cage has teeth 13 extending from the upper 15 and lower 17 surfaces of the cage.

Figure 1D:
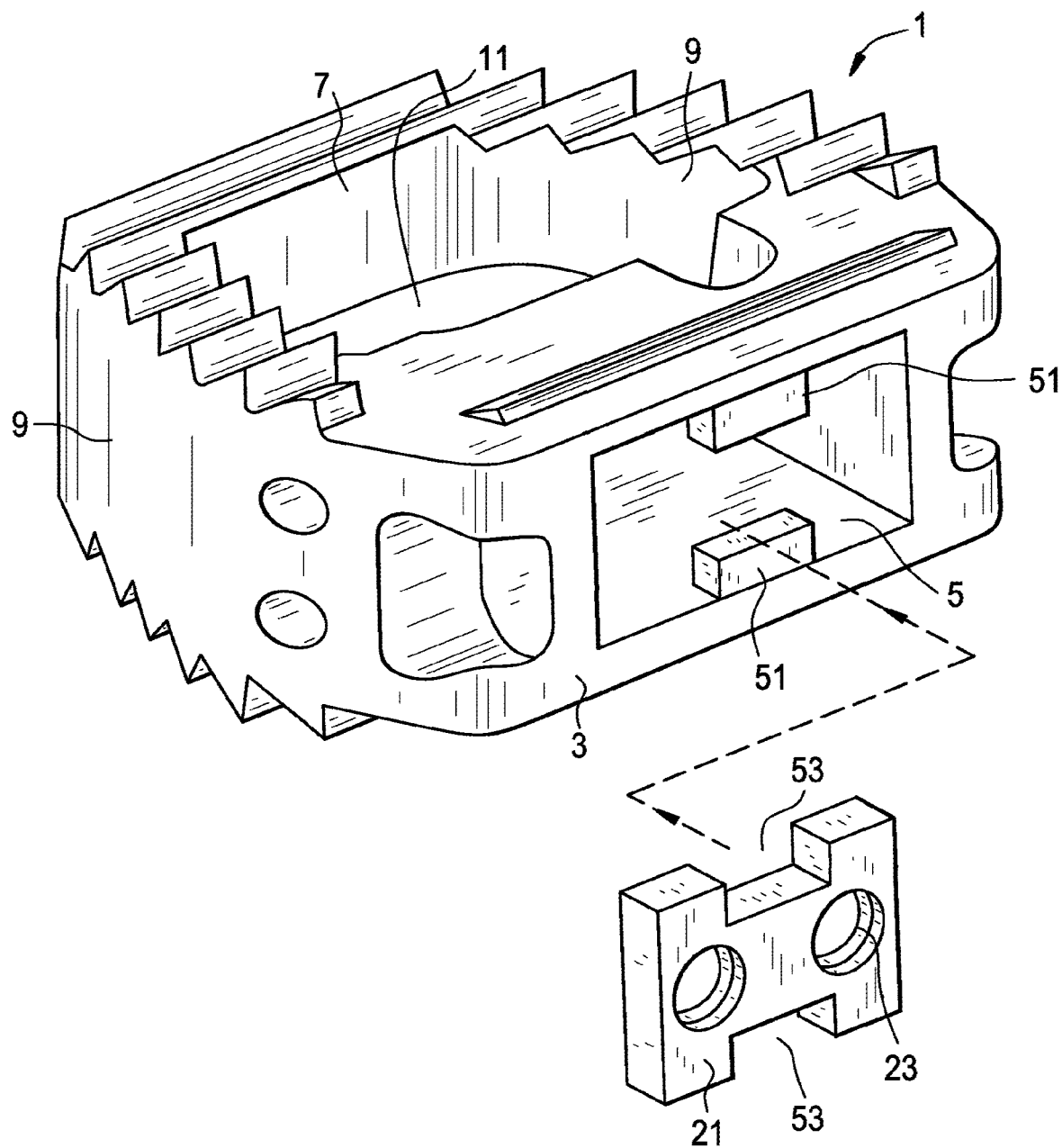
FIG. 1D discloses a cage of the present invention having a moveable faceplate.

Now referring to FIG. 1D, in some embodiments, the peripheries of the faceplate and window having mating features that allow the faceplate to be inserted into the window, and then slightly shifted so that it cannot back out. IN FIG. 1d, the faceplate has a length that is shorter than the corresponding window 5. The periphery of the faceplate has notches 53 that correspond to the protrusions 51 on the periphery of the window. These mating features allow the faceplate to be inserted into the window and past the protrusions. Once, the faceplate so inserted shifts (due to its shorter length), the faceplate may no longer easily be removed from the window.

Figure 2A:
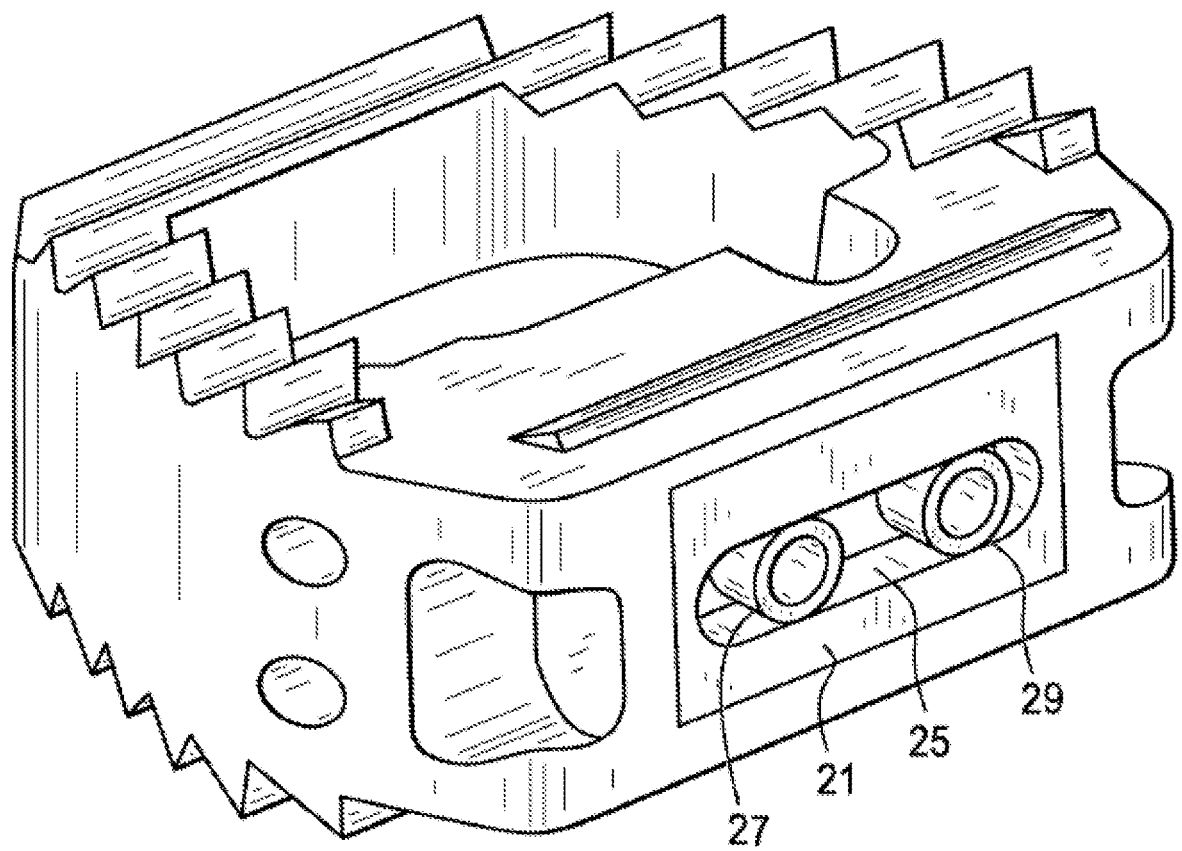
FIG. 2A shows a second combination of the cage having a faceplate attached therethrough.
Figure 2B:
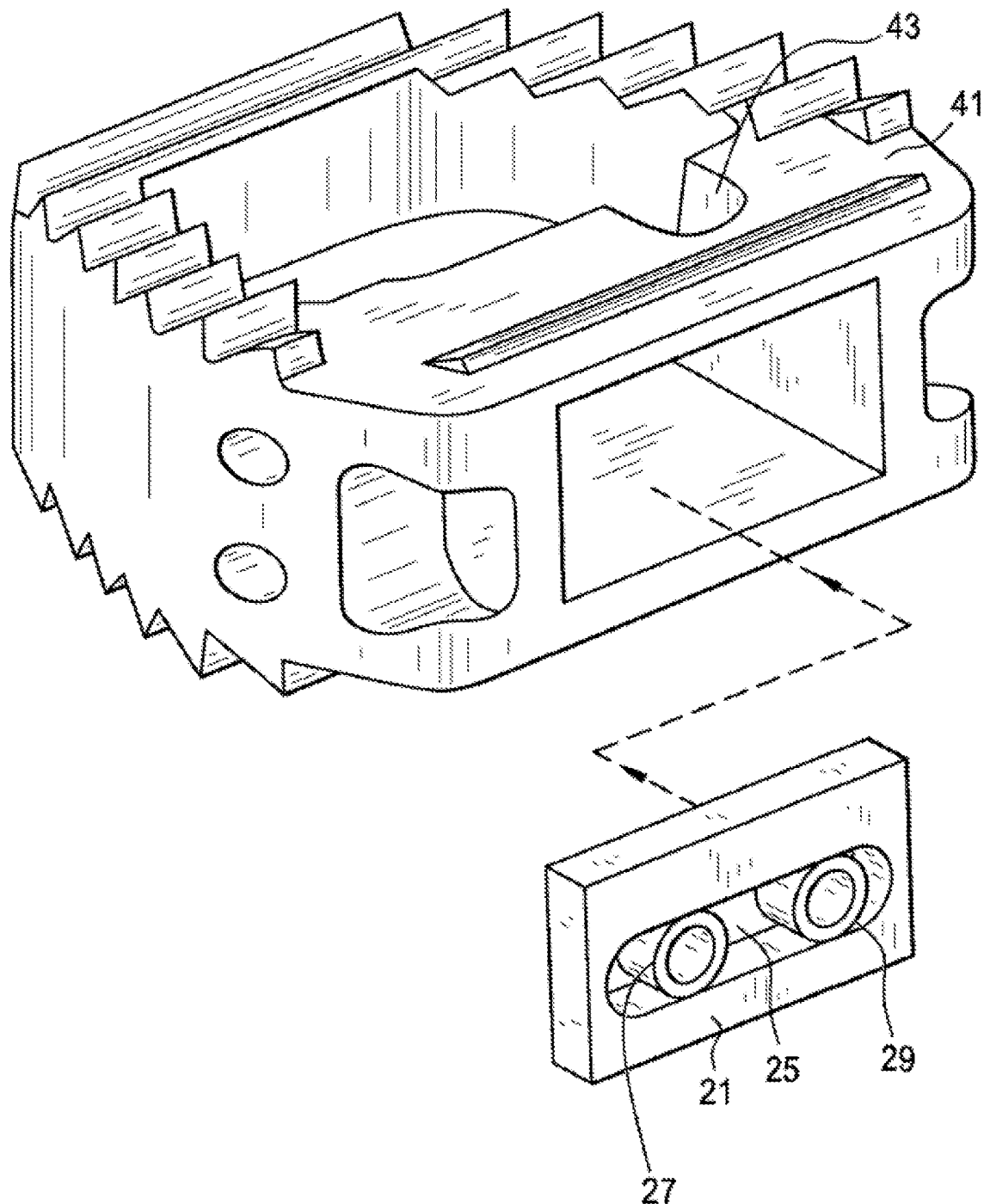
Figure 2C:
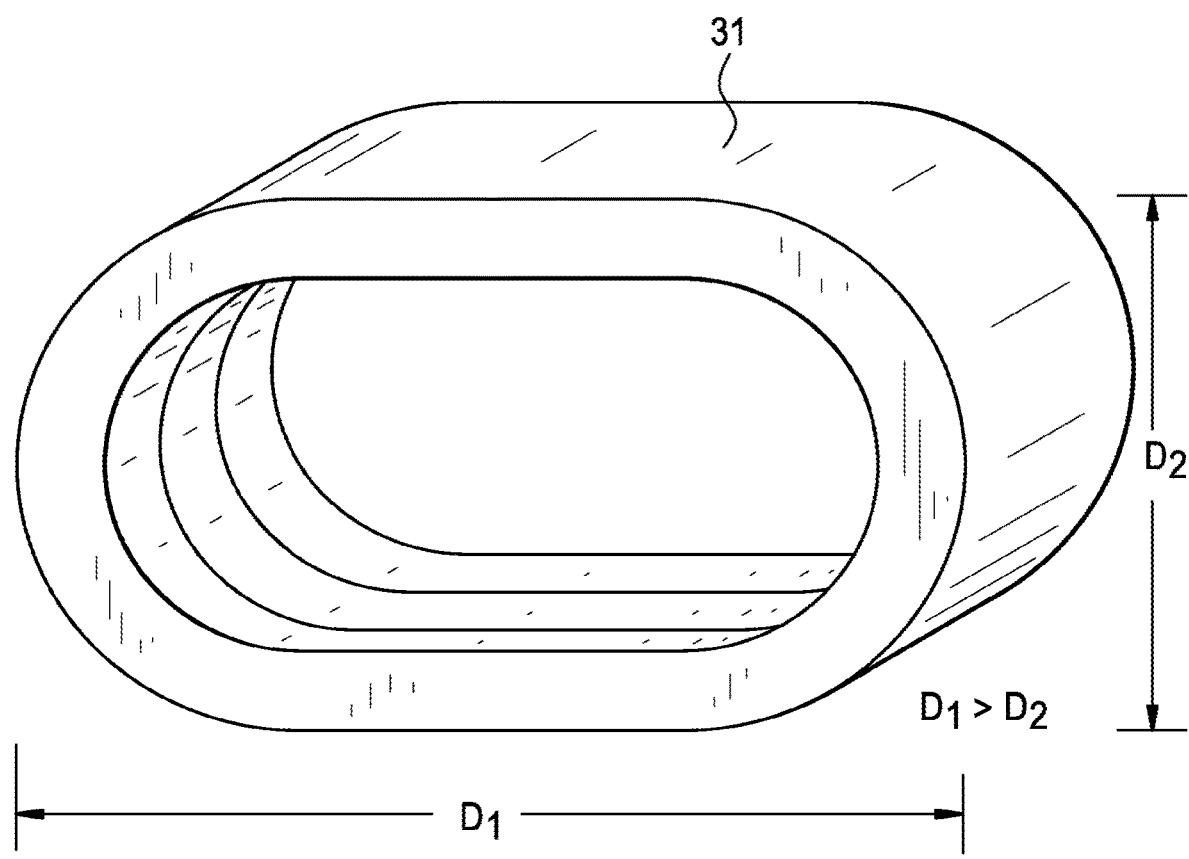
FIG. 2C discloses a non-circular washer.

Also as shown in FIG. 2A-2B, in some embodiments, the face plate has a horizontal slot 25 extending therethrough, with first 27 and second 29 washers received in the slot. The function of the washers is to receive first and second bone screws (not shown) that allow for fixation of the cage. The washers are adapted to be slidable in the slot, so that their positions may be infinitely adjusted to suit the desires of the surgeon. In some embodiments, as in FIG. 2C, at least one (and preferably both) of the washers 31 have a cam shape. This cam shape may provide to the washer a first dimension D1 and a second dimension D2, wherein D1 is greater than D2. This non-circular shape allows the washer to be first slid to an appropriate location within the slot and then turned 90 degrees in order to lock that position. In some embodiments, the washer may have a threaded receiving hole.

In some embodiments (not shown), the there may be three washers disposed in the slot, whereby the two outer washers receive bone fixation means (such as a bone screw) pointing in one direction and the middle washer receives a bone fixation means in the other direction.

In some embodiments (not shown), the there may be four washers disposed in the slot, whereby a first two alternating washers receive bone fixation means (such as a bone screw) pointing in one direction and the remaining two washers each receive a bone fixation means in the other direction.

Now referring to FIG. 2B, in some embodiments, the device comprises first and second screwholes, each screwhole adapted to receive a bone screw. In some of these embodiments, each screwhole is formed in both the plate and the cage. As in FIG. 2B, in some embodiments, each screwhole is at least partially open. In these open embodiments, the front wall comprises a top surface 41 and a bottom surface, wherein a portion 43 of the first screwhole formed in the cage opens at least partially onto the top surface of the cage, and wherein a portion of the second screwhole formed in the cage opens at least partially onto the bottom surface of the cage. The open nature of these allows for the use of larger bone screws within the same cage, thereby enhancing the fixation strength of the device. Lastly, there are preferably first and second bone screws (not shown) respectively received in the first and second screwholes.

In some embodiments, the front wall has a front surface, the face plate has a front surface, and the front surfaces are substantially co-planar. This produces the desirable zero-profile shape that reduces the chances of irritation of the great vessels that sit anterior to the device in the cervical spine.

Figure 3:
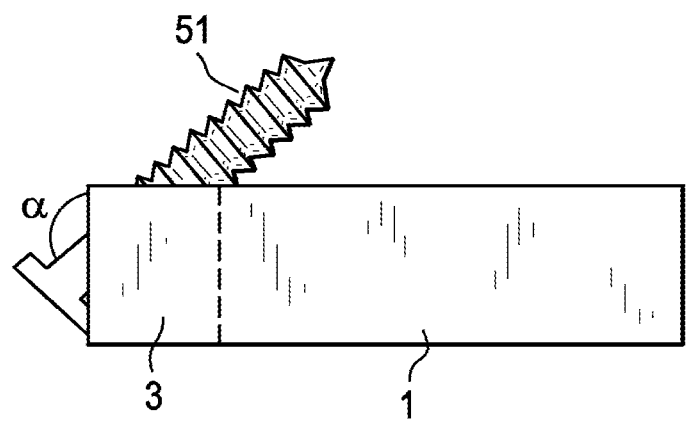
FIG. 3 discloses a bone screw mating with the face plate to produce an angle $\alpha$ of between about 15 and 75 degrees.

In some embodiments, and now referring to FIG. 3, each bone screw 51 preferably mates with the face plate and cage to produce an angle $\alpha$ of between about 15 and 75 degrees.

The faceplate may be attached to the anterior wall of the cage by any conventional means. In some embodiments, the face plate is attached to the front wall by a hinge. In others, the faceplate forms a Morse taper with the window and is attached to the front wall by a press fit mechanism, thereby locking the faceplate in place.

The intervertebral fusion cage of the present invention may be manufactured from any biocompatible flexible material suitable for use in interbody fusion procedures. In some embodiments, the cage comprises a composite comprising 40-100% polyarylethyl ketone PAEK, and optionally 1-60% carbon fiber. Such a cage is radiolucent. Preferably, the polyarylethyl ketone PAEK is selected from the group consisting of polyetherether ketone PEEK, polyether ketone ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. In some embodiments, the composite consists essentially of PAEK and carbon fiber. In some embodiments, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Spine, Raynham, Mass., USA. In some embodiments, the composite is PEEK-OPTIMA™, available from Invibio of Greenville, N.C.

Typically, each of the faceplate and washer is made from a biocompatible metal in order to enhance the strength of the screw-receiving component. In some embodiments, the faceplate is made from a material selected from the group consisting of stainless steel, chromium-cobalt and a titanium alloy.

Typically, each screw is made from a biocompatible metal selected from the group consisting of stainless steel, chromium-cobalt and a titanium alloy.

In some embodiments, a screw is used disclosed as the fixation means for fixing the cage to the vertebral bodies. However, any conventional fixation means for fixing a cage to a vertebral body can be used.

In some embodiments, the fusion cage of the present invention is used to treat DDD and is placed within a disc space between adjacent vertebral bodies. In others, it is used in a corpectomy case, and replaces a vertebral body.

In some embodiments, after the cage of the present invention has been inserted into the disc space, the surgeon may place an endplate preparation instrument (such as a curette) through the anterior window of the cage and prepare the portion of the endplate not supported by bone. This method insures that not only is the endplate adequately prepared, but there remains an intact rim of cortical bone supporting the endplate.

In some embodiments, the device further comprises graft material disposed within the vertical throughole of the cage. In these embodiments, the graft is inserted by a method comprising:
 a) implanting the cage of the present invention into an intervertebral disc space,
 b) inserting bone graft material through the first window of the implanted cage and into the vertical throughhole of the cage, and
 c) attaching a face plate to the front wall of the implanted cage to substantially cover the first window of the cage.

In some embodiments, the bone graft material is injected through the first window. In some embodiments, this bone graft material is flowable. In some embodiments, the flowable graft material may be HEALOS FX™, a flowable collagen-based material available from DePuy Spine of Raynham, Mass., USA.

In other embodiments, the bone graft material is packed into the vertical throughhole.

In some embodiments, the grail material may comprises a bone forming agent. In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and MP-14, including HBGF-1 and HBGF-2; growth differentiation factors (GDFs), members of the hedgehog family of proteins, including indian, sonic and desert hedgehog; ADMP-1; bone-forming members of the interleukin (IL) family; rhGDF-5; and members of the colony-stimulating factor (CSF) family, including CSF-1, G-CSF, and GM-CSF; and isoforms thereof.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP).

BMPs beneficially increasing bone formation by promoting the differentiation of mesenchymal stem cells (MSC) into osteoblasts and their proliferation.

In some embodiments, between about 1 ng and about 10 mg of BMP are administered into the target disc space. In some embodiments, between about 1 microgram (μg) and about 1 mg of BMP are administered into the target disc space.

In many preferred embodiments, the bone forming agent is a porous matrix, and is preferably injectable.

The porous matrix of the present invention may contain porous or semi-porous collagen, extracellular matrices, metals (such as Ti, Ti64, CoCr, and stainless steel), polymers (such as PEEK, polyethylene, polypropylene, and PET) resorbable polymers (such as PLA, PDA, PEO, PEG, PVA, and capralactides), bone substitutes (such as TCP, HA, and CaP), autograft, allograft, xenograft, and/or blends thereof. Matrices may be orientated to enable flow from bony attachment locations to the aspiration port. Matrices may be layered with varying densities, pore structures, materials to enable increase stem filter at desired locations via density, pore size, affinity, as well as fluid flow control (laminar, turbilant, and/or tortuous path).

In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 μm, for example, between about 50 and about 250 μm. In yet other embodiments of the present invention, in situ porosity is produced in the injected matrix to produce a porous scaffold in the interbody space. Once the in situ porosity is produced in the space, the surgeon can inject other therapeutic compounds into the porosity, thereby treating the surrounding tissues and enhancing the remodeling process of the target tissue.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the interbody space.

In another embodiment, the treatment is delivered via injectable absorbable or non-absorbable cement to the target space. The treatment is formulated using bioabsorbable macro-sphere technologies, such that it will allow the release of the bone forming agent. The cement will provide the initial stability required to treat pain in target tissues. These tissues include, but are not limited to, hips, knee, vertebral body and iliac crest. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:

a) a first formulation comprising an acid-soluble type I collagen solution (preferably between about 1 mg/ml and about 7 mg/ml collagen) and b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire can first be embedded in the space, healed to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Specific matrices may be incorporated into the device to provide load bearing qualities, enable directional bone formation, and/or control density of regenerated bone (cortical vs cancellous) or enable cell formation for soft tissue attachment. Nanotubes or nanocrystals can be orientated in a generally axial direction to provide for load bearing abilities as well as capillary wicking of vascular flow to further enhance directional bone formation. Biocompatible nanotubes can currently be produced from either carbon or titanium or hone substitutes including Ca, HA, and TCP.

In one embodiment, the bone forming agent is a plurality of viable ex vivo osteoprogenitor cells. Such viable cells, introduced into the interbody space, have the capability of at least partially supplementing the in situ drawn stem cells in the generation of new bone for the interbody space.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable ex vivo cells are selected as an additional therapeutic agent or substance, the viable cells comprise mesenchymal stem cells (MSCs). MSCs provide a special advantage for administration into the interbody space because it is believed that they can more readily survive the relatively harsh environment present in the space; that they have a desirable level of plasticity; and that they have the ability to proliferate and differentiate into the desired cells.

In some embodiments, the mesenchymal stem cells are obtained from hone marrow, such as autologous bone marrow. In others, the mesenchymal stem cells are obtained from adipose tissue, preferably autologous adipose tissue.

In some embodiments, the mesenchymal stem cells injected into the interbody space are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of Which is incorporated herein by reference in its entirety, can be used. In some embodiments, the matrix used to filter and concentrate the MST's is also administered into the interbody space.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

A matrix may be made from hydrogels or may incorporate a hydrogel as component of the final structure. A hydrogel may be used to expand and enhance filling, improve handling characteristics or increase vacuum pressure. The increased vacuum pressure may be used to determine adequate hydration/stem cell filtration.

In all cases, excess bone marrow aspirate can be collected and mixed with added graft extenders including collagen like the HEALOS™ and HEALOS FX™, each of which is available from DePuy Spine Inc, Raynharn, Mass., USA.

Although the present invention has been described with reference to its preferred embodiments, those skillful in the art will recognize changes that may be made in form and structure which do not depart from the spirit of the invention.

I claim:

1. A method comprising the steps of:
   implanting a cage into an intervertebral disc space that is defined between a first vertebra and a second vertebra, such that an upper wall of the cage faces the first vertebra, and a lower wall opposite the upper wall along a vertical direction faces the second vertebra, and the cage includes 1) a front end and a back end, the front end having a front wall that defines a front surface and a rear surface that faces opposite the front surface, and 2) an aperture that extends through the front wall from the front surface to the rear surface such that the front surface defines an opening to the aperture, the opening to the aperture elongate along a horizontal plane that is perpendicular to the vertical direction, wherein the cage defines a throughhole that extends through the upper and lower walls, the throughhole configured to receive bone graft material, and the cage consists of poly-ether-ether-ketone (PEEK);

threadedly mating a threaded shaft in a threaded receiving hole that extends into a receiving member, the receiving member is supported by a face plate that is supported by the cage, and the receiving member extends into a hole that extends through the face plate, and wherein the receiving member defines a front opening to the threaded receiving hole, and the method further comprises the step of inserting the threaded shaft into the aperture; and moving the front opening to the threaded receiving hole along the horizontal plane.

2. The method of claim 1, wherein the cage defines first and second aperture ends of the aperture along the horizontal plane.

3. The method of claim 1, wherein the cage is configured to receive an endplate preparation instrument through the aperture.

4. The method of claim 1, wherein the receiving member comprises a washer.

5. The method of claim 1, wherein the faceplate closes a portion less than an entirety of the aperture.

6. The method of claim 1, wherein the moving step comprises moving the receiving member along the horizontal plane.

7. The method of claim 6, wherein the front wall defines first and second aperture sides of the aperture, and the moving step comprises translating the face plate along the cage to a position whereby both 1) the face plate is spaced from the first aperture side in a direction toward the second aperture side with respect to a view of the cage and the face plate that is oriented in a direction from the front surface to the rear surface, and 2) the face plate is spaced from the second aperture side in a direction toward the first aperture side with respect to the view.

8. The method of claim 1, wherein the front opening to the threaded receiving hole is not recessed in the receiving member.

9. A method comprising the steps of:
implanting a cage into an intervertebral disc space that is defined between a first vertebra and a second vertebra, such that an upper wall of the cage faces the first vertebra, and a lower wall opposite the upper wall along a vertical direction faces the second vertebra, and the cage includes 1) a front end and a back end, the front end having a front wall that defines a front surface and a rear surface that faces opposite the front surface, and 2) an aperture that extends through the front wall from the front surface to the rear surface such that the front surface defines an opening to the aperture, the opening to the aperture elongate along a horizontal plane that is perpendicular to the vertical direction;

inserting bone graft material into a throughhole of the cage that extends through the upper and lower walls;

threadedly mating a threaded shaft in a threaded receiving hole that extends into a receiving member, wherein the receiving member defines a front opening to the threaded receiving hole, and the implanting step further comprises inserting the threaded shaft into the aperture, wherein the receiving member is supported by a face plate that is supported by the cage, and the receiving member extends into a hole that extends through the face plate; and moving the front opening to the threaded receiving hole along the horizontal plane.

10. The method of claim 9, wherein the receiving member comprises a washer.

11. The method of claim 9, wherein the faceplate closes a portion less than an entirety of the aperture.

12. The method of claim 9, wherein the moving step comprises moving the receiving member along the horizontal plane.

* * * * *